(12) United States Patent
Morita et al.

(10) Patent No.: US 9,018,424 B2
(45) Date of Patent: Apr. 28, 2015

(54) METHOD OF PRODUCING DIOL OR TRIOL

(75) Inventors: Izumi Morita, Kamakura (JP); Masateru Ito, Kamakura (JP); Hideki Sawai, Kamakura (JP); Shinichi Minegishi, Urayasu (JP); Katsushige Yamada, Kamakura (JP); Kenji Kawamura, Kamakura (JP); Shinichi Yamane, Tokyo (JP)

(73) Assignee: Toray Industries, Inc., Tokyo (JP)

( * ) Notice: Subject to any disclaimer, the term of this patent is extended or adjusted under 35 U.S.C. 154(b) by 344 days.

(21) Appl. No.: 13/076,053

(22) Filed: Mar. 30, 2011

(65) Prior Publication Data
US 2012/0253082 A1  Oct. 4, 2012

(51) Int. Cl.
*C07C 29/76* (2006.01)
*C07C 31/20* (2006.01)

(52) U.S. Cl.
CPC ..................................... *C07C 29/76* (2013.01)

(58) Field of Classification Search
CPC .... C07C 29/80; C07C 31/202; C07C 31/205; C07C 31/207; C07C 31/22; C07C 31/225
USPC .......................................... 568/868, 869, 871
See application file for complete search history.

(56) References Cited

U.S. PATENT DOCUMENTS

| | | | | |
|---|---|---|---|---|
| 2,234,400 A | * | 3/1941 | van de Griendt et al. ........ | 203/78 |
| 4,806,244 A | * | 2/1989 | Guilhem ........................ | 210/638 |
| 4,857,363 A | * | 8/1989 | Sasaki et al. .................. | 427/245 |
| 6,187,197 B1 | * | 2/2001 | Haddock ....................... | 210/641 |
| 2005/0069997 A1 | | 3/2005 | Adkesson et al. | |
| 2006/0065600 A1 | | 3/2006 | Sunkara et al. | |
| 2007/0193960 A1 | | 8/2007 | Frank et al. | |
| 2010/0041925 A1 | * | 2/2010 | Reimann et al. .............. | 568/868 |
| 2010/0145108 A1 | * | 6/2010 | Traving et al. ................ | 568/868 |
| 2011/0003355 A1 | * | 1/2011 | Clark et al. ................... | 435/158 |

FOREIGN PATENT DOCUMENTS

| | | | |
|---|---|---|---|
| GB | 2437516 A | * | 10/2007 |
| JP | 62-201606 A | | 9/1987 |
| JP | 63-316744 A | | 12/1988 |
| JP | 05-153982 A | | 6/1993 |
| JP | 06-030790 A | | 2/1994 |
| JP | 2010-150248 | * | 7/2010 |

OTHER PUBLICATIONS

Matsuo, Y., et al,, "Determination of Residual Glucose, Hydroxymethylfurfural and Oligosaccharides in Acid-hydrolyzates of Glucose." Journal of Fermentation Technology, vol. 39, No. 5, pp. 256-262, 1961.
Ben-David et al., "Mechanism and Role of Partitioning in Removal of Organics by RO and NF Composite Membranes", Desalination, vol. 199, pp. 49-51, 2006.
Ben-David et al., "Thermodynamic Factors in Partitioning and Rejection of Organic Compounds by Polymide Composite Membranes", Environ. Sci. Technol., vol. 40, pp. 7023-7028, 2006.
Branco et al., "Sharpless Asymmetric Dihydroxylation of Olefins in Water-Surfactant Media with Recycling of the Catalytic System by Membrane Nanofiltration", Adv. Synth. Catal., pp. 2086-2098, 2008.

* cited by examiner

*Primary Examiner* — Rosalynd Keys
(74) *Attorney, Agent, or Firm* — Birch, Stewart, Kolasch & Birch, LLP (57) ABSTRACT

A method for producing a diol or triol, which has a step of removing impurities contained in a diol- or triol-containing solution, is provided. In the method, a diol- or triol-containing solution is filtered through a nanofiltration membrane having a polyamide-containing functional layer. The diol- or triol-containing solution is then collected from the permeate flow of the nanofiltration membrane.

5 Claims, 1 Drawing Sheet

METHOD OF PRODUCING DIOL OR TRIOL

BACKGROUND OF THE INVENTION

1. Field of the Invention

The present invention relates to a method for producing a diol or triol, which method comprises a step of removing impurities from a diol- or triol-containing solution.

2. Description of the Related Art

Diols and triols are compounds which are industrially very important as raw materials of polymers and as raw materials of pharmaceutical agents. Diols such as butanediol and ethylene glycol produce polyesters when they are copolymerized with dicarboxylic acids such as terephthalic acid and adipic acid. Further, glycerin, which is a trial, is used as a raw material of cosmetics and the like. It is well known that these dials and triols can be produced by chemical synthesis, but, in recent years, since they can be produced by biochemical methods such as fermentation methods and enzymatic methods, they are drawing attention as nonpetroleum biopolymer materials. Therefore, technologies by which such dials and triols can be produced at high purity and at high efficiency have been demanded.

In general, as the method for purifying dials and trials, solvent extraction or distillation is employed. In solvent extraction, in cases where the desired product is a lower alcohol, which is highly soluble in water, distribution of the lower alcohol into the organic phase is difficult, so that use of a special extraction solvent or multistep extraction may be required, leading to increase in the cost (Patent Document 1). Further, in purification by distillation, if impurities are contained, distillation residues are generated, leading to decrease in the yield. Further, diol- and triol-containing liquids prepared by the fermentation method contain sugars, which are nutrient sources of microorganisms, and organic acids and proteins, which are metabolites, and these are reported to yield colored impurities by heating (Non-patent Document 1). Therefore, in order to carry out purification of highly pure dial or triol and highly efficient production thereof, removal of impurities in the fermentation broth is very important.

As methods for producing highly pure diol or triol, a method for producing 1,3-propanediol wherein distillation purification is carried out in combination with microfiltration, ultrafiltration, nanofiltration or ion exchange (Patent Document 2); and a method for separating diol using a reverse osmosis membrane or a nanofiltration membrane (Patent Document 3) are disclosed. However, they do not disclose the effect of difference in the material of the nanofiltration membrane on the permeation selectivity and on purity of the diol or triol after the purification.

PRIOR ART REFERENCES

Patent Documents

Patent Document 1 US 2007/193960 A
Patent Document 2 US2005/069997 A
Patent Document 3 US2006/065600 A

Non-Patent Documents

Non-patent Document 1 Yoshiyuki MATSUO, Determination of Residual Glucose: Journal of Fermentation Technology, 39, 5, 256-262 (1961)

SUMMARY OF THE INVENTION

In view of the above-mentioned purpose, that is, purification of a diol or trial, the present invention aims to provide a method by which a dial or trial can be separated and recovered more efficiently at higher purity than by the conventional methods.

The present inventors intensively studied to solve the above problems and discovered that a high-purity dial or triol can be obtained by filtering a diol- or trial-containing solution through a nanofiltration membrane having a functional layer containing a polyamide, and that the distillation yield can be effectively increased by this process, thereby completing the present invention.

That is, the present invention is constituted by the following (1) to (7).

(1) A method of producing at least one type of diols or at least one type of triols, said method comprising the steps of: filtering a solution containing said at least one type of diols or at least one type of triols solution through a nanofiltration membrane having a polyamide-containing functional layer; and collecting the diol- or triol-containing solution from the permeate flow of said nanofiltration membrane.

(2) The method according to (1), wherein said dial is ethylene glycol, 1,3-propanediol, 2,3-butanediol, 1,4-butanediol or 1,3-butanediol.

(3) The method according to (1), wherein said triol is glycerin or butanetriol.

(4) The method according to (1), wherein said polyamide comprises a cross-linked piperazine polyamide as a major component, and a constituting component represented by Formula [I]:

wherein R represents —H or —CH$_3$, and n represents an integer of 0 to 3.

(5) The method according to (1), further comprising the step of filtering the collected diol- or triol-containing solution through a reverse osmosis membrane to increase the diol or triol concentration.

(6) The method according to (1), further comprising the step of distilling the collected diol or triol-containing solution under a pressure of not less than 1 Pa and not more than atmospheric pressure, at a temperature of not less than 25° C. and not more than 200° C.

(7) The method according to (1), further comprising the step of distilling the concentrated diol or triol solution after filtration through said reverse osmosis membrane under a pressure of not less than 1 Pa and not more than atmospheric pressure, at a temperature of not less than 25° C. and not more than 200° C.

By the present invention, metal catalysts, inorganic salts, sugars and/or proteins existing in a diol- or triol-containing chemically synthesized reaction solution or fermentation broth can be removed by a simple process, and therefore the distillation yield can be increased, so that a highly pure diol or triol can be produced highly efficiently.

DESCRIPTION OF SYMBOLS IN DRAWINGS

1 Feed tank
2 Cell equipped with nanofiltration membrane or reverse osmosis membrane
3 High-pressure pump
4 Permeate Flow which has pass through membrane
5 Retentate Flow which has been concentrated with membrane
6 Feed flow sent by high-pressure pump
7 90φ Nanofiltration membrane or reverse osmosis membrane
8 Supporting plate

BEST MODE FOR CARRYING OUT THE INVENTION

The present invention will now be described more concretely.

In the method of the present invention for producing a dial or trial, the dial or triol is separated from a diol- or trial-containing solution, and the present invention relates to a method for producing a diol or triol, comprising a step of allowing the diol- or triol-containing solution to pass through a nanofiltration membrane to remove metal catalysts, inorganic salts, sugars, proteins and/or the like to obtain a dial or trial solution, and a step of allowing the diol or triol solution obtained by the above step to be fed into a reverse osmosis membrane to concentrate the solution, followed by distilling the resulting concentrate.

In the present invention, the term "dial" means a compound having two hydroxyl groups (OH groups) in the molecule and having no other functional groups, and the "diol" is not restricted as long as the molecule is within this scope. In the present invention, a diol may comprise a single type of diol or may be a mixture of plural types of diols. The dial in the present invention is preferably a dial having 1 to 6 carbon atoms, and particular examples thereof include linear aliphatic compounds such as methylene glycol, ethylene glycol, 1,2-propanediol, 1,3-propanediol, 1,2-butanediol, 1,3-butanediol, 1,4-butanediol, 2,3-butanediol and 1,5-pentanediol; branched aliphatic saturated compounds such as isobutylene glycol; aromatic compounds such as catechol and resorcinol; and unsaturated compounds such as propenediol and butenediol.

In the present invention, the term "triol" means a compound having three hydroxyl groups (OH groups) in the molecule and having no other functional groups, and the "triol" is not restricted as long as the molecule is within this scope. In the present invention, a triol may comprise a single type of trial or may be a mixture of plural types of triols. The triol in the present invention is preferably a triol having 1 to 6 carbon atoms, and particular examples thereof include aliphatic compounds such as glycerin, butanetriol, pentanetriol, hexanetriol, trimethylol propane; and aromatic compounds such as pyrogallol, hydroxyhydroquinone and phloroglucinol; among which glycerin is more preferred.

The method for producing a diol- or triol-containing solution used in the present invention is not restricted as long as it is known to those skilled in the art, and, in cases where a chemical synthesis method is used, examples of the method include synthesis of 1,2-propanediol by asymmetric reduction as described in JP 63-316744 A, and a method for producing glycerin via an allyl alcohol or acrolein using propylene as a starting material. Further, in cases where fermentation culture of a microorganism is employed, examples of the method include the method for producing glycerin as described in JP 5-153982 A, and the method for producing 1,2-propanediol as described in JP 6-30790 A. The method used in the present invention for producing a diol- or triol-containing solution is preferably fermentation culture of a microorganism, and, in such a case, the fermentation broth itself containing a diol or triol can be used as the diol- or triol-containing solution to be applied to the nanofiltration membrane.

The nanofiltration membrane used in the present invention is also called NF membrane, and generally defined as a "membrane that allows permeation of monovalent ions but blocks divalent ions". The membrane is considered to have voids of as small as several nanometers, and mainly used for rejection microparticles, molecules, ions, salts and/or the like in water.

By filtering a diol- or triol-containing solution is filtered through a nanofiltration membrane, impurities (substances other than diols and triols) are removed at the feed flow and the diol- or triol-containing solution is collected from the permeate flow.

Examples of known materials constituting the functional layer of nanofiltration membranes generally include polymer materials such as cellulose acetate polymers; polyamides; polyesters; polyimides; and vinyl polymers; and, in the present invention, a nanofiltration membrane having a functional layer comprising a polyamide is used since a high purification efficiency can be attained therewith. Other plural membrane materials may also be contained in the functional layer comprising a polyamide, but the functional layer preferably comprises a polyamide as a major component. In the present specification, in cases where the nanofiltration membrane is specified by a material, the nanofiltration membrane has a functional layer comprising the material unless otherwise specified.

In terms of the membrane structure, either an asymmetric membrane wherein at least one side of the membrane has a dense layer, which membrane has micropores having a diameter that gradually increases from the dense layer to the inside of the membrane or to the other side of the membrane, or a composite membrane having on the dense layer of an asymmetric membrane a very thin functional layer formed by another material can be used. Examples of the composite membrane which may be used include the composite membrane described in JP 62-201606 A, wherein a nanofiltration membrane having a polyamide-containing functional layer was placed on a support membrane made of a polysulfone membrane material.

The nanofiltration membrane having a polyamide-containing functional layer (hereinafter also referred to as polyamide nanofiltration membrane) used in the present invention is preferably a composite membrane having a high pressure resistance, a high permeability and a high solute removal performance. Further, in order to allow maintenance of durability against the operation pressure, a high permeability and a high rejection performance, the membrane preferably has a structure wherein the polyamide-containing functional layer is held by a support made of a porous membrane and/or a non-woven fabric.

In the polyamide nanofiltration membrane, preferred examples of the carboxylic acid component, expressed in terms of monomers, constituting the polyamide include aromatic carboxylic acids such as trimesic acid, benzophenone tetracarboxylic acid, trimellitic acid, pyromellitic acid, isophthalic acid, terephthalic acid, naphthalenedicarboxylic acid, diphenylcarboxylic acid and pyridinecarboxylic acid, and, in view of solubility to the film-forming solvent, trimesic acid, isophthalic acid or terephthalic acid, or a mixture thereof is more preferred.

Preferred examples of the amine component, expressed in terms of monomers, constituting the polyamide include primary diamines having an aromatic ring(s), such as m-phenylenediamine, p-phenylenediamine, benzidine, methylenebisdianiline, 4,4'-diaminobiphenyl ether, dianisidine, 3,3', 4-triaminobiphenyl ether, 3,3',4,4'-tetraminobiphenyl ether, 3,3'-dioxybenzidine, 1,8-naphthalenediamine, m(p)-monomethylphenylenediamine, 3,3'-monomethylamino-4, 4'-diaminobiphenyl ether, 4,N,N'-(4-aminobenzoyl)-p(m)-phenylenediamine-2,2'-bis(4-aminophenyl benzimidazol), 2,2'-bis(4-aminophenyl benzoxazol), 2,2'-bis(4-aminophenyl benzothiazole); and secondary diamines such as piperazine and piperidine and derivatives thereof; and, in particular, a nanofiltration membrane having a functional layer composed of a cross-linked polyamide containing piperazine or piperidine as monomers has a high pressure resistance and durability as well as heat resistance and chemical resistance, and is therefore preferably used. The polyamide more preferably comprises a cross-linked piperazine polyamide or a cross-linked piperidine polyamide as a major component and further comprises a constituting component represented by the Formula [I]; still more preferably comprises a cross-linked piperazine polyamide as a major component and further comprises a constituting component represented by the Formula [I]. Further, preferably, in the Formula [I], n=3. Examples of the nanofiltration membrane having a functional layer comprising a cross-linked piperazine polyamide as a major component and further comprising a constituting component represented by the Formula [I] include the one described in JP 62-201606 A, and particular examples of the nanofiltration membrane include a cross-linked piperazine polyamide nanofiltration membrane UTC60 manufactured by TORAY INDUSTRIES, INC., which has a functional layer comprising a cross-linked piperazine polyamide as a major component and further comprising a constituting component represented by the Formula [I] wherein n=3.

The polyamide nanofiltration membrane used in the present invention may be in an appropriate form such as a spiral-wound membrane, flat membrane or hollow fiber membrane module, and is preferably used as a spiral-wound membrane module. Particular examples of the nanofiltration membrane which may be used include SU-210, SU-220, SU-600 and SU-610, which are nanofiltration modules manufactured by TORAY INDUSTRIES, INC. containing UTC60 manufactured by the same manufacturer, which nanofiltration modules have a polyamide functional layer comprising a cross-linked piperazine polyamide as a major component and further a constituting component represented by the Formula [I]. Further particular examples of the membrane include flat membranes, such as nanofiltration membranes NF-45, NF-90, NF-200 and NF-400 manufactured by FilmTec Corporation, which have a functional layer made of a cross-linked piperazine polyamide, and nanofiltration membranes NF99, NF97 and NF99HF manufactured by Alfa-Laval, which have a polyamide functional layer, and membrane modules using these membrane materials.

In the present invention, the filtration of a diol- or trial-containing solution through a nanofiltration membrane may be carried out under pressure. With a filtration pressure lower than 0.1 MPa, the membrane permeation flux decreases, and with a filtration pressure higher than 8 MPa, the membrane is damaged. Therefore, the filtration pressure is preferably within the range of 0.1 MPa to 8 MPa, and, in cases where it is within the range of 0.5 MPa to 7 MPa, the membrane permeation flux is high, so that the diol- or trial-containing solution can be allowed to pass through the membrane efficiently with less possibility of causing damage to the membrane, which is more preferred. A filtration pressure of 1 MPa to 6 MPa is especially preferred.

In the present invention, in the filtration of a diol- or triol-containing solution through a nanofiltration membrane, the recovery of the diol or triol can be increased by returning the retentate to the feed solution and repeating the filtration. The recovery of the diol or triol can be calculated by measuring the total amount of the diol or triol contained before the nanofiltration and the total amount of the diol or triol permeated through the nanofiltration membrane, followed by calculation by Equation 1.

Recovery of diol or triol (%)=(total amount of diol or triol which has permeated through nanofiltration membrane/total amount of diol or triol contained before nanofiltration)×100 (Equation 1).

In terms of the membrane separation performance of the nanofiltration membrane used in the present invention, the membrane preferably shows a salt removal rate of not less than 45% when an aqueous sodium chloride solution (500 mg/L) at 25° C., pH 6.5 is filtered under a filtration pressure of 0.75 MPa. Here, the salt removal rate can be calculated by measuring the salt concentration of the permeated aqueous sodium chloride solution, followed by calculation by Equation 2.

Salt removal rate=100×{1−(salt concentration of permeate/salt concentration of feed solution) (Equation 2).

Further, in terms of the permeation performance of the nanofiltration membrane, the membrane preferably shows a membrane permeation flux $(m^3/(m^2 \cdot day))$ of not less than 0.3 with an aqueous sodium chloride solution (500 mg/L) under a filtration pressure of 0.3 MPa. The membrane permeation flux can be calculated by measuring the amount of the permeant, the length of time required for collecting this amount of the permeant, and the membrane area, followed by calculation by Equation 3.

Membrane permeation flux $(m^3/(m^2 \cdot day))$=amount of permeant/(membrane area×collection time) (Equation 3).

In the present invention, examples of the impurities separated from the diol- or triol-containing solution into the retentate by the nanofiltration membrane include inorganic substances such as calcium, sodium, sulfuric acid, nitric acid and phosphoric acid; sugars such as glucose, fructose, xylose, sucrose, galactose and starch; and proteins; and mixtures thereof can also be preferably separated.

The permeability of the nanofiltration membrane to a diol- or triol-containing solution in the present invention can be evaluated by calculating the permeation rate of the dial or triol. The permeation rate of the dial or trial can be calculated by measuring the concentration of the dial or trial (dial or triol concentration of feed solution) contained in the feed solution (diol- or triol-containing liquid) and the concentration of the dial or trial (dial or trial concentration of permeate) contained in the permeate (dial or triol solution) by analysis represented by high performance liquid chromatography and gas chromatography, followed by calculation by Equation 4.

Permeation rate of diol or triol (%)=(dial or triol concentration of permeate/diol or triol concentration of feed solution)×100 (Equation 4).

The permeate from the nanofiltration membrane is preferably concentrated in cases where the concentration of the substance of interest is low, since, in such cases, the later-mentioned distillation step requires a large amount of energy to remove water, which has a lower boiling point than dials and triols. In terms of the method for concentrating the permeate from the nanofiltration membrane, methods using a concentrator represented by an evaporator are commonly employed and also applicable to the present invention, but, since the heat capacity of water is much larger than those of organic solvents, enormous energy and time are required for the concentration. On the other hand, concentration by a reverse osmosis membrane is superior to concentration using an evaporator in view of reduction in the energy/cost, and therefore preferably applied to the present invention.

The reverse osmosis membrane in the present invention is a filter for removing ions and/or low molecular-weight molecules using a pressure difference larger than the osmotic pressure of the liquid to be treated as the driving force, and examples thereof which can be used include cellulose membranes such as those made of cellulose acetate and membranes wherein a multifunctional amine compound and a multifunctional acid halide were polycondensed to provide a separation functional layer made of a polyamide on a microporous support membrane. In order to suppress dirt, that is, fouling, on the surface of the reverse osmosis membrane, a low-fouling reverse osmosis membrane, which is mainly for sewage treatment, can also be preferably employed, which reverse osmosis membrane is prepared by covering the surface of a separation functional layer made of a polyamide with an aqueous solution of a compound having at least one reactive group reactive with an acid halide group, thereby allowing acid halide groups remaining on the surface the separation functional layer to form covalent bonds with the reactive groups. Since most of the divalent ions are successfully removed in the step of filtering through the nanofiltration membrane of the present invention, stable membrane concentration can be carried out without formation of scale on the surface of the reverse osmosis membrane.

Further, the term "filtering through the reverse osmosis membrane" means that the diol- or triol-containing solution which has permeated through the nanofiltration membrane is concentrated by being allowed to pass through the reverse osmosis membrane, followed by collecting the resulting solution containing a diol or triol in the retentate flow.

Examples of the reverse osmosis membrane preferably used in the present invention include composite membranes having a cellulose acetate polymer as a functional layer (hereinafter referred to as cellulose acetate reverse osmosis membranes) and composite membranes having a polyamide functional layer (hereinafter referred to as polyamide reverse osmosis membranes). Here, examples of the cellulose acetate polymer include polymers prepared with organic acid esters of cellulose such as cellulose acetate, cellulose diacetate, cellulose triacetate, cellulose propionate and cellulose butyrate, which may be used solely, as a mixture, or as a mixed ester. Examples of the polyamide include linear polymers and cross-linked polymers constituted by aliphatic and/or aromatic diamine monomers. Examples of the form of the membrane which may be used as appropriate include the flat membrane, spiral-wound membrane and hollow fiber membrane.

Particular examples of the reverse osmosis membrane used in the present invention include polyamide reverse osmosis membrane modules manufactured by TORAY INDUSTRIES, INC., such as low-pressure type modules SU-710, SU-720, SU-720F, SU-710L, SU-720L, SU-720LF, SU-720R, SU-710P and SU-720P, as well as high-pressure type modules SU-810, SU-820, SU-820L and SU-820FA containing UTC70 as the reverse osmosis membrane; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D manufactured by Nitto Denko Corporation; RO98pHt, 8099, HR98PP and CE4040C-30D manufactured by Alfa-Laval; GE Sepa manufactured by GE; and BW30-4040, TW30-4040, XLE-4040, LP-4040, LE-4040, SW30-4040 and SW30HRLE-4040 manufactured by FilmTec Corporation.

In the present invention, filtration of the permeate from the nanofiltration membrane with the reverse osmosis membrane is carried out under pressure, and the filtration pressure is preferably within the range of 1 MPa to 8 MPa since, with a filtration pressure lower than 1 MPa, the membrane permeation flux decreases, and with a filtration pressure higher than 8 MPa, the membrane is damaged. Further, since, with a filtration pressure within the range of 1 MPa to 7 MPa, the membrane permeation flux is high, the diol or triol solution can be efficiently concentrated. The filtration pressure is most preferably within the range of 2 MPa to 6 MPa since there is less possibility of causing damage to the membrane in this case.

Further, in the present invention, by subjecting the concentrate of the permeate from the nanofiltration membrane to the step of distillation, a highly pure diol or triol can be obtained. The distillation step is carried out preferably under a reduced pressure of not less than 1 Pa and not more than atmospheric pressure (normal pressure, about 101 kPa), more preferably under a reduced pressure of not less than 100 Pa and not more than 15 kPa. In cases where the distillation is carried out under reduced pressure, the distillation temperature is preferably 20° C. to 200° C., more preferably 50° C. to 150° C.

EXAMPLES

The present invention will now be described more concretely by way of Examples, but the present invention is not restricted to the Examples below.

Reference Example 1

Evaluation of Permeability of Nanofiltration Membrane to Diol and Triol

To 10 L of ultrapure water, 10 g of ethylene glycol, 1,3-propanediol, 2,3-butanediol, glycerin, 1,3-butanediol or 1,4-butanediol (all of which were manufactured from Wako Pure Chemical Industries, Ltd.) was added, and the resulting mixture was stirred at 25° C. for 1 hour, thereby preparing 1000 ppm aqueous diol or trial solution. Subsequently, 10 L of the thus prepared aqueous diol or triol solution was fed to a feed tank 1 of the membrane filtration apparatus shown in FIG. 1. As the 90φ nanofiltration membrane indicated by Symbol 7 in FIG. 2, each of a cross-linked piperazine polyamide nanofiltration membrane "UTC60" (nanofiltration membrane 1; manufactured by TORAY INDUSTRIES, INC.), a polyamide nanofiltration membrane "NF99" (nanofiltration membrane 2, manufactured by Alfa-Laval), a cross-linked piperazine polyamide nanofiltration membrane "NF-400" (nanofiltration membrane 3; manufactured by FilmTec Corporation), a cellulose acetate nanofiltration membrane "GE Sepa" (nanofiltration membrane 4; manufactured by GE Osmonics) and a polyamide nanofiltration membrane "NF99HF" (nanofiltration membrane 5; manufactured by Alfa-Laval) was placed in a cell 2 made of stainless steel (SUS316), and the temperature of the feed solution was adjusted to 25° C. and the pressure of a high-pressure pump 3 was adjusted to 1 MPa, followed by collecting the permeate 4. The concentration of dial contained in each of the feed tank 1 and the permeate 4 was analyzed with a gas chromatography: GC-2010 (manufactured by Shimadzu Corporation) under the following conditions, thereby calculating the permeation rate of the dial.

Column: TC-1, 0.53 mm I.D.×15 m, df=1.5 μm (GL Science); Mobile phase: helium gas (7.9 mL/min., 50 to 100° C.: 5° C./min.); Detection: FID 250° C.

Further, the glycerin concentration was calculated using "F-kit Glycerin" (manufactured by J. K. International Inc.) based on the amount of change in the absorbance at UV 340 nm, to calculate the permeation rate of glycerin. The results are shown in Table 1.

To 10 L of ultrapure water, 10 g of magnesium sulfate (manufactured by Wake Pure Chemical Industries, Ltd.) was added, and the resulting mixture was stirred at 25° C. for 1 hour, to prepare 1000 ppm aqueous magnesium sulfate solution. Subsequently 10 L of the prepared aqueous magnesium sulfate solution was fed to the feed tank 1, followed by collecting the permeate from each of the nanofiltration membranes 1 to 4 under the same conditions as in Reference Example 1. The concentration of magnesium sulfate in each of the feed tank 1 and the permeate 4 was analyzed with an ion chromatography (manufactured by Dionex Corporation)

TABLE 1

| | Product name (manufacturer name)/ membrane material | Diol or triol | Feed (ppm) | Permeate (ppm) | Permeation rate (%) |
|---|---|---|---|---|---|
| Nanofiltration membrane 1 | UTC60 (TORAY INDUSTRIES, INC.)/ Cross-linked piperazine polyamide | Ethylene glycol | 1000 | 721 | 72.1 |
| | | 1,3-Propanediol | 1000 | 298 | 29.8 |
| | | 2,3-Butanediol | 1000 | 388 | 38.8 |
| | | Glycerin | 1000 | 321 | 32.1 |
| | | 1,3-Butanediol | 1000 | 355 | 35.5 |
| | | 1,4-Butanediol | 1000 | 564 | 56.4 |
| Nanofiltration membrane 2 | NF99 (Alfa-Laval)/ Polyamide | Ethylene glycol | 1000 | 733 | 73.3 |
| | | 1,3-Propanediol | 1000 | 263 | 26.3 |
| | | 2,3-Butanediol | 1000 | 394 | 39.4 |
| | | Glycerin | 1000 | 436 | 43.6 |
| | | 1,3-Butanediol | 1000 | 315 | 31.5 |
| | | 1,4-Butanediol | 1000 | 463 | 46.3 |
| Nanofiltration membrane 3 | NF-400 (FilmTec Corporation)/ Cross-linked piperazine polyamide | Ethylene glycol | 1000 | 702 | 70.2 |
| | | 1,3-Propanediol | 1000 | 321 | 32.1 |
| | | 2,3-Butanediol | 1000 | 355 | 35.5 |
| | | Glycerin | 1000 | 421 | 42.1 |
| | | 1,3-Butanediol | 1000 | 410 | 41.0 |
| | | 1,4-Butanediol | 1000 | 544 | 54.4 |
| Nanofiltration membrane 4 | GE Sepa (GE Osmonics)/ Cellulose acetate | Ethylene glycol | 1000 | 696 | 69.6 |
| | | 1,3-Propanediol | 1000 | 208 | 20.8 |
| | | 2,3-Butanediol | 1000 | 423 | 42.3 |
| | | Glycerin | 1000 | 369 | 36.9 |
| | | 1,3-Butanediol | 1000 | 390 | 39.0 |
| | | 1,4-Butanediol | 1000 | 583 | 58.3 |
| Nanofiltration membrane 5 | NF99HF (Alfa-Laval)/ Polyamide | Ethylene glycol | 1000 | 802 | 80.2 |
| | | 1,3-Propanediol | 1000 | 348 | 34.8 |
| | | 2,3-Butanediol | 1000 | 413 | 41.3 |
| | | Glycerin | 1000 | 466 | 46.6 |
| | | 1,3-Butanediol | 1000 | 397 | 39.7 |
| | | 1,4-Butanediol | 1000 | 515 | 51.5 |

As shown by the results in Table 1, the diols and triol permeated through any of the nanofiltration membranes. Further, the permeation rate varied among the compounds, and ethylene glycol showed the highest permeation rate. In terms of the other compounds, the effect of difference in the membrane material contained in the functional layer was small.

Reference Example 2

Evaluation of Rejection Rate of Nanofiltration Membrane against Inorganic Salt (Magnesium Sulfate)

under the following conditions, thereby calculating the rejection rate of the magnesium sulfate.

Anion; column (AS4A-SC (manufactured by Dionex Corporation)), eluent (1.8 mM sodium carbonate/1.7 mM sodium hydrogen carbonate), temperature (35° C.).

Cation; column (CS12A (manufactured by Dionex Corporation)), eluent (20 mM methanesulfonic acid), temperature (35° C.).

The results are shown in Table 2,

TABLE 2

| | Product name (manufacturer name)/ membrane material | Filtration pressure (MPa) | Magnesium sulfate concentration in feed (ppm) | Magnesium sulfate concentration in permeate (ppm) | Magnesium sulfate rejection rate (%) |
|---|---|---|---|---|---|
| Nanofiltration membrane 1 | UTC60 (TORAY INDUSTRIES, INC.)/ Cross-linked piperazine polyamide | 1 | 1000 | 2 | 99.8 |

TABLE 2-continued

|  | Product name (manufacturer name)/ membrane material | Filtration pressure (MPa) | Magnesium sulfate concentration in feed (ppm) | Magnesium sulfate concentration in permeate (ppm) | Magnesium sulfate rejection rate (%) |
|---|---|---|---|---|---|
| Nanofiltration membrane 2 | NF99 (Alfa-Laval)/ Polyamide | 1 | 1000 | 20 | 98.0 |
| Nanofiltration membrane 3 | NF-400 (FilmTec Corporation)/ Cross-linked piperazine polyamide | 1 | 1000 | 20 | 98.0 |
| Nanofiltration membrane 4 | GE Sepa (GE Osmonics)/ Cellulose acetate | 1 | 1000 | 30 | 97.0 |
| Nanofiltration membrane 5 | NF99HE (Alfa-Laval)/ Polyamide | 1 | 1000 | 20 | 98.0 |

From the results in Table 2, it was shown that UTC60 (nanofiltration membrane 1: manufactured by TORAY INDUSTRIES, INC.) shows the highest rejection rate against the inorganic salt, and that, compared to the polyamide nanofiltration membranes (nanofiltration membranes 1 to 3), the cellulose acetate nanofiltration membrane GE Sepa (nanofiltration membrane 4) shows a lower removal rate of magnesium sulfate. Thus, it was suggested that dials and triols can be purified at higher efficiency when a polyamide nanofiltration membrane is used.

Examples 1 to 9

Purification of 1,3-Propanediol from Fermentation Broth Using Nanofiltration Membrane
<Preparation of 1,3-Propanediol-Containing Broth>
A budding yeast strain NBRC10505 was cultured as follows. In terms of the culture medium, 2 L of a culture medium containing 60 g/L Yutosei (manufactured by MUSO Co., Ltd.) and 1.5 g/L ammonium sulfate was prepared and then autoclaved (121° C., 15 minutes).

First, the yeast NBRC10505 strain was cultured overnight with shaking in a test tube containing 5 ml of the culture medium (pre-preculture). The pre-preculture broth was inoculated to 100 ml of a fresh lot of the medium, and culture was carried out in a 500-ml Sakaguchi flask for 24 hours with shaking (preculture). Culture was carried out while adjusting temperature and pH. The operating conditions of the jar fermenter were as shown below.

Reaction vessel volume (amount of medium), 2 (L); temperature adjustment, 30 (° C.); ventilation volume for the reaction vessel, 0.2 (L/min.); stirring rate of the reaction vessel, 400 rpm; pH adjustment, adjusted to pH 5 with 1 N calcium hydroxide. After 24 hours of the culture, the broth was centrifuged to remove the yeast cells, and the supernatant was collected. To this broth, 1,3-propanediol was added to 20 g/L.
<Purification with Nanofiltration Membrane>

Figure 1:
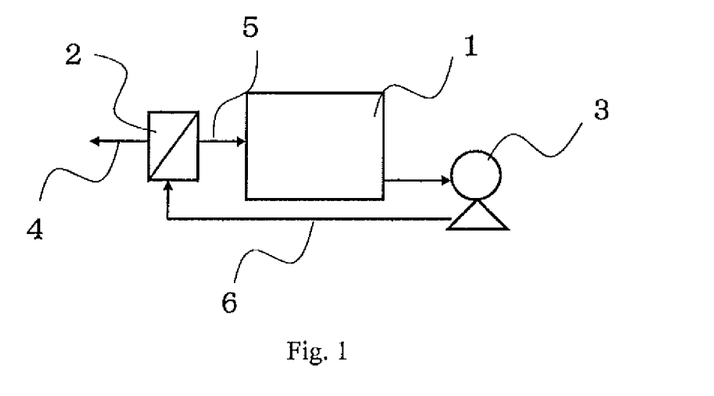
FIG. 1 is a schematic view showing an embodiment of the separation apparatus used in the present invention having a nanofiltration membrane and a reverse osmosis membrane.
Figure 2:
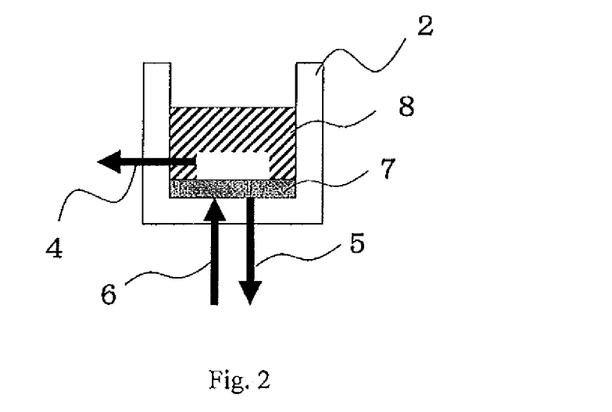
FIG. 2 is a schematic view showing an embodiment of a cross-sectional view of a cell in the separation apparatus used in the present invention having a nanofiltration membrane and a reverse osmosis membrane, which cell has the reverse osmosis membrane attached thereto.

Thereafter, 2 L of the culture supernatant obtained as described above was fed to the feed tank 1 of the membrane filtration apparatus shown in FIG. 1. As the 90φ nanofiltration membrane indicated by Symbol 7 in FIG. 2, each of the above nanofiltration membranes 1 to 3 was placed in a cell made of stainless steel (SUS316), and the pressure by the high-pressure pump 3 was adjusted to 1 MPa, 3 MPa or 5 MPa, followed by collecting the permeate 4 for the respective pressures. The concentration of 1,3-proopanediol contained in each of the liquid tank 1 and the permeate 4 was analyzed under the same conditions as those in Reference Example 1 using a gas chromatography (manufactured by Shimadzu Corporation). Further, the sulfate ion concentration was analyzed with an ion chromatography (manufactured by Dionex Corporation) under the same conditions as in Reference Example 2. Further, the sugar concentration (glucose, fructose and sucrose) was analyzed with a high performance liquid chromatography (manufactured by Shimadzu Corporation) under the following conditions.
Column: Luna 5u NH₂ 100A (manufactured by Phenomenex, Inc.), 30° C.
Mobile phase: water:acetonitrile=1:3, 0.6 mL/min.
Detector: RI.

The results are shown in Table 3.

TABLE 3

|  | Nanofiltration membrane | Filtration pressure (MPa) | Flux (m³/m²/day) | Sulfate ion concentration | | | 1,3-Propanediol concentration | | | Total sugar concentration | | |
|---|---|---|---|---|---|---|---|---|---|---|---|---|
|  |  |  |  | Feed (ppm) | Permeate (ppm) | Rejection rate (%) | Feed (g/L) | Permeate (g/L) | Permeation rate (%) | Feed (g/L) | Permeate (g/L) | Rejection rate (%) |
| Example 1 | Nanofiltration membrane 1 | 1 | 1.62 | 873 | 11 | 98.7 | 20 | 5.8 | 29.0 | 15 | 0.8 | 95.0 |
| Example 2 |  | 3 | 4.83 | 873 | 5 | 99.4 | 20 | 5.3 | 26.3 | 15 | 0.6 | 96.0 |
| Example 3 |  | 5 | 7.29 | 873 | 3 | 99.7 | 20 | 4.8 | 24.1 | 15 | 0.5 | 97.0 |
| Example 4 | Nanofiltration membrane 2 | 1 | 2.03 | 958 | 20 | 97.9 | 20 | 5.3 | 26.3 | 17 | 0.7 | 96.0 |
| Example 5 |  | 3 | 5.83 | 958 | 19 | 98.0 | 20 | 4.8 | 24.0 | 17 | 0.5 | 97.0 |
| Example 6 |  | 5 | 8.54 | 958 | 15 | 98.4 | 20 | 4.7 | 23.5 | 17 | 0.5 | 97.0 |
| Example 7 | Nanofiltration membrane 3 | 1 | 2.12 | 905 | 24 | 97.3 | 20 | 5.6 | 28.0 | 17 | 0.7 | 96.0 |
| Example 8 |  | 3 | 5.42 | 905 | 21 | 97.7 | 20 | 4.8 | 24.0 | 17 | 0.5 | 97.0 |
| Example 9 |  | 5 | 8.23 | 905 | 17 | 98.1 | 20 | 4.2 | 21.0 | 17 | 0.5 | 97.0 |

As shown in Table 3, with all the nanofiltration membranes and under all the filtration pressures, sulfate ion and the sugars were removed and a 1,3-propanediol solution was obtained. Further, the other impurities were also mostly removed from the brown-colored broth, and a colorless transparent solution was obtained. Further, compared to the separation properties of the nanofiltration membrane disclosed in Table 7 of US2005/069997, Examples 1 to 9 showed remarkably superior removal capacities for sulfate ion and sugars.

Further, an operation in which 1.5 L of the permeate was collected and 1.5 L of distilled water was added thereto, followed by collecting the permeate again was repeated four times in order to increase the recovery of 1,3-propanediol. As a result, not less than 55% of 1,3-propanediol in the broth could be recovered.

<Distillation from Solution Concentrated Using Reverse Osmosis Membrane>

Among the clean 1,3-propanediol solutions obtained as described above, those of Example 2, Example 5, Example 8 and Example 11 were subjected to the study. To the feed tank 1 of the membrane filtration apparatus shown in FIG. 1, 5.5 L of the solution was fed. As the 90φ reverse osmosis membrane indicated by Symbol 7 in FIG. 2, a polyamide reverse osmosis membrane (UTC-70, manufactured by TORAY INDUSTRIES, INC.) was attached to a cell made of stainless steel (SUS316), and membrane filtration was carried out by adjusting the pressure by the high-pressure pump 3 to 3 MPa and the temperature of the feed solution to 35° C., thereby removing 5.4 L of the permeate 4 from the reverse osmosis membrane. One hundred milliliters of the thus obtained concentrate was subjected to distillation under reduced pressure (5 mmHg). The results of the distillation are shown in Table 4.

TABLE 4

| | Nanofiltration membrane | 1,3-Propanediol concentration (g/L) Before concentration | 1,3-Propanediol concentration (g/L) After concentration | Distillation yield (%) | GC purity (%) |
|---|---|---|---|---|---|
| Example 2 | Nanofiltration membrane 1 | 5.0 | 274 | 95 | 99.7 |
| Example 5 | Nanofiltration membrane 2 | 4.5 | 248 | 92 | 99.5 |
| Example 8 | Nanofiltration membrane 3 | 4.5 | 248 | 90 | 99.5 |

From these results, it was shown that the present method allows efficient production of high-purity 1,3-propanediol.

Comparative Example 1

Purification of 1,3-Propanediol by Using Active Carbon and Ion-Exchange

In the same manner as in Example 1, 2 L of a 1,3-propanediol-containing broth was prepared. The broth was treated with 20 g of active carbon, and allowed to pass through an ion-exchange resin (IRA-140:IR-120=2:1) to desalt the solution. The 1,3-propanediol-containing solution was concentrated using a reverse osmosis membrane, and then subjected to distillation under reduced pressure (5 mmHg), in the same manner as in the above Example 1. As a result, the distillation yield was 76%, and the GC purity was 94.5%. The decrease in the distillation yield was considered to be due to a large amount the remaining residue. Further, since 4.2 g/L of glucose was detected in the concentrate, it was assumed that impurities derived from sugars decreased the GC purity.

Comparative Examples 2 to 4

Purification of 1,3-Propanediol with Cellulose Acetate Nanofiltration Membrane

In the same manner as in Example 1, 2 L of a 1,3-propanediol-containing broth was prepared. Subsequently, a cellulose acetate nanofiltration membrane "GE Sepa" (nanofiltration membrane 4) was placed in a cell made of stainless steel, and the permeate 4 under a pressure of 1 MPa, 3 MPa or 5 MPa was collected as in the above Examples, followed by filtration. The results of analysis of the permeates are shown in Table 5.

TABLE 5

| | Nanofiltration membrane | Filtration pressure (MPa) | Flux (m³/m²/day) | Sulfate ion concentration | | | 1,3-Propanediol concentration | | | Total sugar concentration | | |
|---|---|---|---|---|---|---|---|---|---|---|---|---|
| | | | | Feed (ppm) | Permeate (ppm) | Rejection rate (%) | Feed (g/L) | Permeate (g/L) | Permeation rate (%) | Feed (g/L) | Permeate (g/L) | Rejection rate (%) |
| Comparative Example 2 | Nanofiltration membrane 4 | 1 | 1.19 | 916 | 30 | 96.7 | 20 | 4.2 | 20.8 | 15 | 0.9 | 94.0 |
| Comparative Example 3 | | 3 | 3.75 | 916 | 25 | 97.3 | 20 | 3.7 | 18.4 | 15 | 0.8 | 95.0 |
| Comparative Example 4 | | 5 | 4.64 | 916 | 19 | 97.9 | 20 | 2.9 | 14.3 | 15 | 0.5 | 97.0 |

Thus, the cellulose acetate nanofiltration membrane showed a lower permeation rate of 1,3-propanediol as well as lower removal rates of sulfate ion/sugars compared to polyamide nanofiltration membranes. Further, when the permeate obtained in Comparative Examples 3 was subjected to concentration with a reverse osmosis membrane and distillation under reduced pressure in the same manner as in the above Example 1, the distillation yield was 88% and the GC purity was 99.0%, indicating that a cellulose acetate nanofiltration membrane shows a lower purification efficiency than a polyamide nanofiltration membrane.

Examples 10 to 14

Purification of Ethylene Glycol, 2,3-Butanediol, Glycerin, 1,3-Butanediol or 1,4-Butanediol from Fermentation Broth Using Nanofiltration Membrane In the same manner as in Example 1, 2 L each of 20 g/L ethylene glycol-containing broth, 2,3-butanediol-containing broth, glycerin-containing broth, 1,3-butanediol-containing broth and 1,4-butanediol-containing broth was prepared. Each of these was fed to the feed tank 1 of the membrane filtration apparatus. As the 90φ nanofiltration membrane indicated by Symbol 7 in FIG. 2, the nanofiltration membrane 1 (UTC60) was placed in a cell made of stainless steel (SUS316), and the pressure of the high-pressure pump 3 was adjusted to 3 MPa, followed by collecting the permeate 4. The concentration of ethylene glycol, 2,3-butanediol, 1,3-butanediol or 1,4-butanediol in each of the feed solution and the permeate was measured by gas chromatography in the same manner as in the above Example 1. The glycerin concentration was measured using F-kit in the same manner as in Reference Example 1. The inorganic salt concentration and sugar concentration were measured by high performance liquid chromatography in the same manner as in the method described in Example 1. The results are shown in Table 6.

As shown in Table 7, in any of the cases, a highly pure diol or triol was obtained at high yield. Therefore, it was shown that the present invention may increase the yield of the diol or trial.

TABLE 6

| | Nanofiltration membrane | Filtration pressure (MPa) | Target | Flux (m³/m²/day) | Sulfate ion concentration | | | Concentration of desired compound | | | Total sugar concentration | | |
|---|---|---|---|---|---|---|---|---|---|---|---|---|---|
| | | | | | Feed (ppm) | Permeate (ppm) | Rejection rate (%) | Feed (g/L) | Permeate (g/L) | Permeation rate (%) | Feed (g/L) | Permeate (g/L) | Rejection rate (%) |
| Example 10 | Nanofiltration membrane 1 | 3 | Ethylene glycol | 4.99 | 923 | 4 | 99.6 | 20 | 13.1 | 65.7 | 15 | 0.8 | 95.0 |
| Example 11 | Nanofiltration membrane 1 | 3 | 2,3-Butanediol | 4.83 | 896 | 5 | 99.4 | 20 | 7.0 | 35.1 | 18 | 0.7 | 96.0 |
| Example 12 | Nanofiltration membrane 1 | 3 | Glycerin | 4.62 | 914 | 3 | 99.7 | 20 | 6.8 | 34.2 | 14 | 0.4 | 97.0 |
| Example 13 | Nanofiltration membrane 1 | 3 | 1,3-Butanediol | 3.16 | 832 | 2 | 99.8 | 20 | 5.0 | 25.1 | 15 | 0.7 | 95.5 |
| Example 14 | Nanofiltration membrane 1 | 3 | 1,4-Butanediol | 3.44 | 844 | 3 | 99.6 | 20 | 6.2 | 30.8 | 14 | 0.6 | 95.8 |

As shown in Table 6, with any of the compounds, sulfate ion and sugars were removed, and a clean diol- or triol-containing solution was obtained.

Subsequently, the diol- or triol-containing solution was concentrated using a reverse osmosis membrane, and then subjected to distillation under reduced pressure (5 mmHg), in the same manner as in the above Example 1. The results are shown in Table 7.

| | Target | Concentration of desired compound (g/L) | | Distillation yield (%) | GC purity (%) |
|---|---|---|---|---|---|
| | | Before concentration | After concentration | | |
| Example 10 | Ethylene glycol | 12.4 | 679 | 96 | 99.5 |
| Example 11 | 2,3-Butanediol | 6.6 | 363 | 91 | 99.5 |
| Example 12 | Glycerin | 6.4 | 354 | 88 | 99.8 |
| Example 13 | 1,3-Butanediol | 4.7 | 259 | 94 | 99.8 |
| Example 14 | 1,4-Butanediol | 5.8 | 321 | 96 | 99.8 |

Comparative Examples 5 and 6

Purification of 1,3-Butanediol or 1,4-Butanediol with Cellulose Acetate Nanofiltration Membrane In the same manner as in Example 1, 2 L each of a 1,3-butanediol-containing broth and 1,4-butanediol-containing broth was prepared. Subsequently, a cellulose acetate nanofiltration membrane "GE Sepa" (nanofiltration membrane 4) was placed in a cell made of stainless steel, and the permeate 4 was collected at 3 MPa in the same manner as in the above Examples, thereby carrying out filtration. This permeate was analyzed in the same manner. The results are shown in Table 8.

TABLE 8

| | Nanofiltration membrane | Filtration pressure (MPa) | Target | Flux (m³/m²/day) | Sulfate ion concentration | | | Concentration of desired compound | | | Total sugar concentration | | |
|---|---|---|---|---|---|---|---|---|---|---|---|---|---|
| | | | | | Feed (ppm) | Permeate (ppm) | Rejection rate (%) | Feed (g/L) | Permeate (g/L) | Permeation rate (%) | Feed (g/L) | Permeate (g/L) | Rejection rate (%) |
| Comparative Example 5 | Nanofiltration membrane 4 | 3 | 1,3-Butanediol | 2.21 | 832 | 30 | 96.4 | 20 | 5.6 | 28.1 | 15 | 0.9 | 94.0 |
| Comparative Example 6 | | 3 | 1,4-Butanediol | 2.41 | 844 | 25 | 97.0 | 20 | 7.9 | 39.7 | 14 | 0.7 | 95.0 |

Thus, it was revealed that, compared to the case of purification with the polyamide nanofiltration membrane shown in Examples 13 and 14, the cellulose acetate nanofiltration membrane shows a higher permeation rate of 1,3-butanediol and 1,4-butanediol but lower removal rates of sulfate ion/sugars. Therefore, these permeates were subjected to concentration with a reverse osmosis membrane and distillation under reduced pressure as in the above Example 1. As a result, 1,3-butanediol showed a distillation yield of 85% and GC purity of 98.4%, and 1,4-butanediol showed a distillation yield of 87% and GC purity of 98.9%. Thus, it was shown that the cellulose acetate nanofiltration membrane shows lower purification efficiencies than the polyamide nanofiltration membrane.

What is claimed is:

1. A method of producing at least one butanediol, said method comprising the steps of:
    filtering a solution containing said at least one butanediol through a nanofiltration membrane having a polyamide-containing functional layer; and
    collecting butanediol-containing solution from the permeate flow of said nanofiltration membrane;
wherein said butanediol is 2,3-butanediol, 1,4-butanediol or 1,3-butanediol.

2. The method according to claim 1, wherein said polyamide comprises a cross-linked piperazine polyamide as a major component, and said piperazine polyamide is formed from a constituting component represented by Formula [I]:

wherein R represents —H or —CH$_3$, and n represents an integer of 0 to 3.

3. The method according to claim 1, further comprising the step of filtering the collected butanediol-containing solution through a reverse osmosis membrane to increase the diol concentration.

4. The method according to claim 1, further comprising the step of distilling the collected butanediol-containing solution under a pressure of not less than 1 Pa and not more than atmospheric pressure, and at a temperature of not less than 25° C. and not more than 200° C.

5. The method according to claim 3, further comprising the step of distilling the concentrated butanediol solution after filtration through said reverse osmosis membrane under a pressure of not less than 1 Pa and not more than atmospheric pressure, and at a temperature of not less than 25° C. and not more than 200° C.

\* \* \* \* \*